United States Patent [19]
Ochel

[11] Patent Number: 5,970,981
[45] Date of Patent: Oct. 26, 1999

[54] MOUTHGUARD MADE AT LEAST PARTIALLY FROM AN EDIBLE CANDY

[76] Inventor: George M. Ochel, 376 Madison Ave., New Milford, N.J. 07646

[21] Appl. No.: 09/141,059

[22] Filed: Aug. 27, 1998

[51] Int. Cl.⁶ .................................................. A61C 5/14
[52] U.S. Cl. ........................................ 128/859; 128/861
[58] Field of Search ................... 128/846, 848, 128/859–862; 602/902

[56] References Cited

U.S. PATENT DOCUMENTS

| | | |
|---|---|---|
| 2,190,231 | 2/1940 | Craddock . |
| 4,944,313 | 7/1990 | Katz et al. . |
| 4,949,731 | 8/1990 | Harding . |
| 5,318,043 | 6/1994 | Burr et al. . |
| 5,323,787 | 6/1994 | Pratt ........................................ 128/859 |
| 5,365,945 | 11/1994 | Halstrom ................................. 128/859 |
| 5,385,155 | 1/1995 | Kittelsen ................................. 128/861 |
| 5,409,016 | 4/1995 | Bloodsaw . |
| 5,582,187 | 12/1996 | Hussey . |
| 5,657,765 | 8/1997 | Est . |
| 5,819,744 | 10/1998 | Stoyka ..................................... 128/859 |

Primary Examiner—Michael A. Brown
Attorney, Agent, or Firm—Richard M. Goldberg

[57] ABSTRACT

A mouthguard includes a U-shaped upper bite plate which removably fits over upper teeth of a person, the upper bite plate including an upper lingual side, an upper buccal side and a lower side which connects together the upper lingual and buccal sides in a U-shaped cross-sectional configuration, the lower side having a lower exposed surface, and the entire upper bite plate being made from a soft, deformable and edible gummi candy; and a U-shaped lower bite plate which removably fits over lower teeth of the person, the lower bite plate including a lower lingual side, a lower buccal side and an upper side which connects together the lower lingual and buccal sides in a U-shaped cross-sectional, the upper side having an upper exposed surface, and the entire lower bite plate being made from a soft, deformable and edible gummi candy.

14 Claims, 3 Drawing Sheets

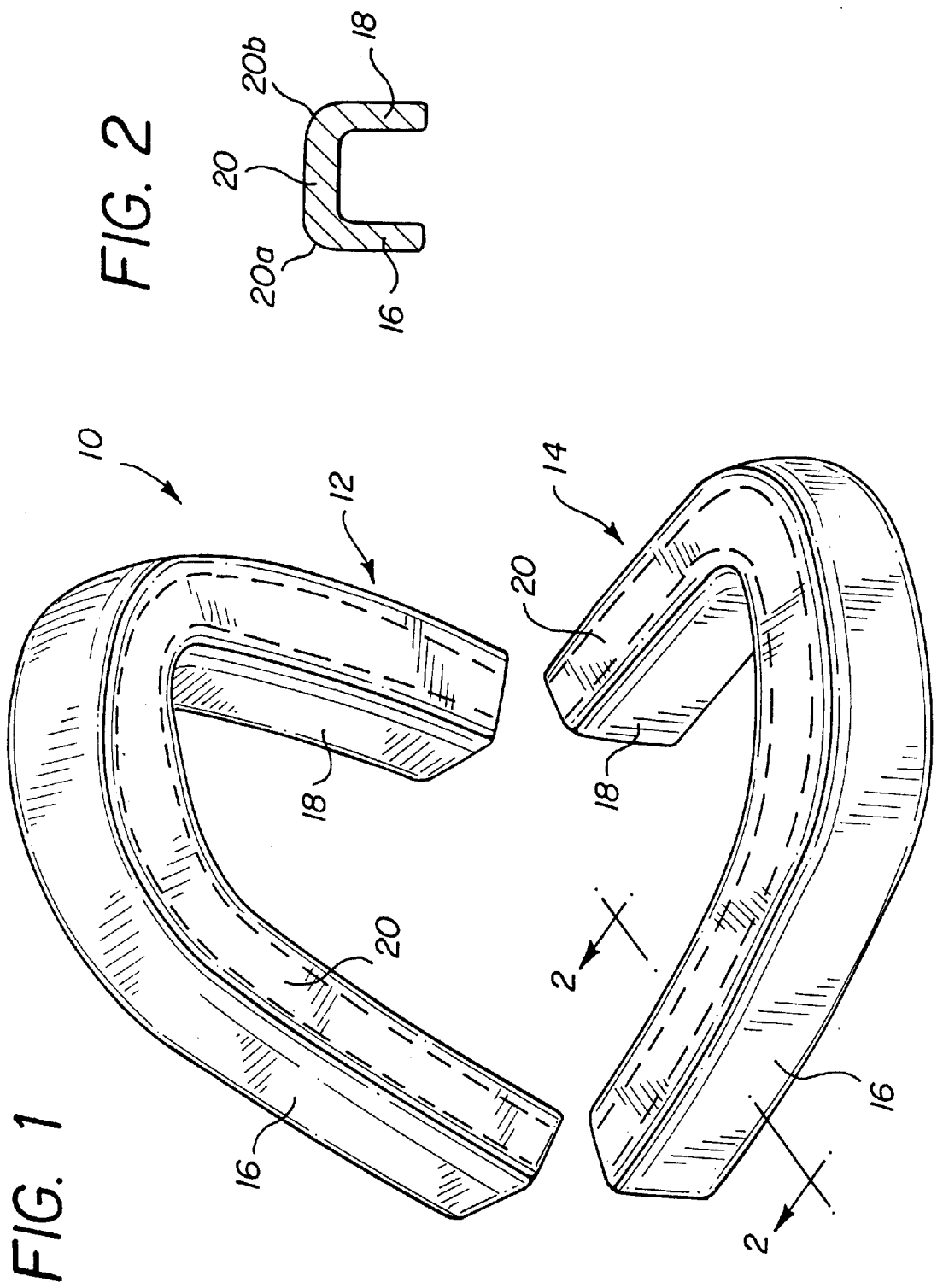

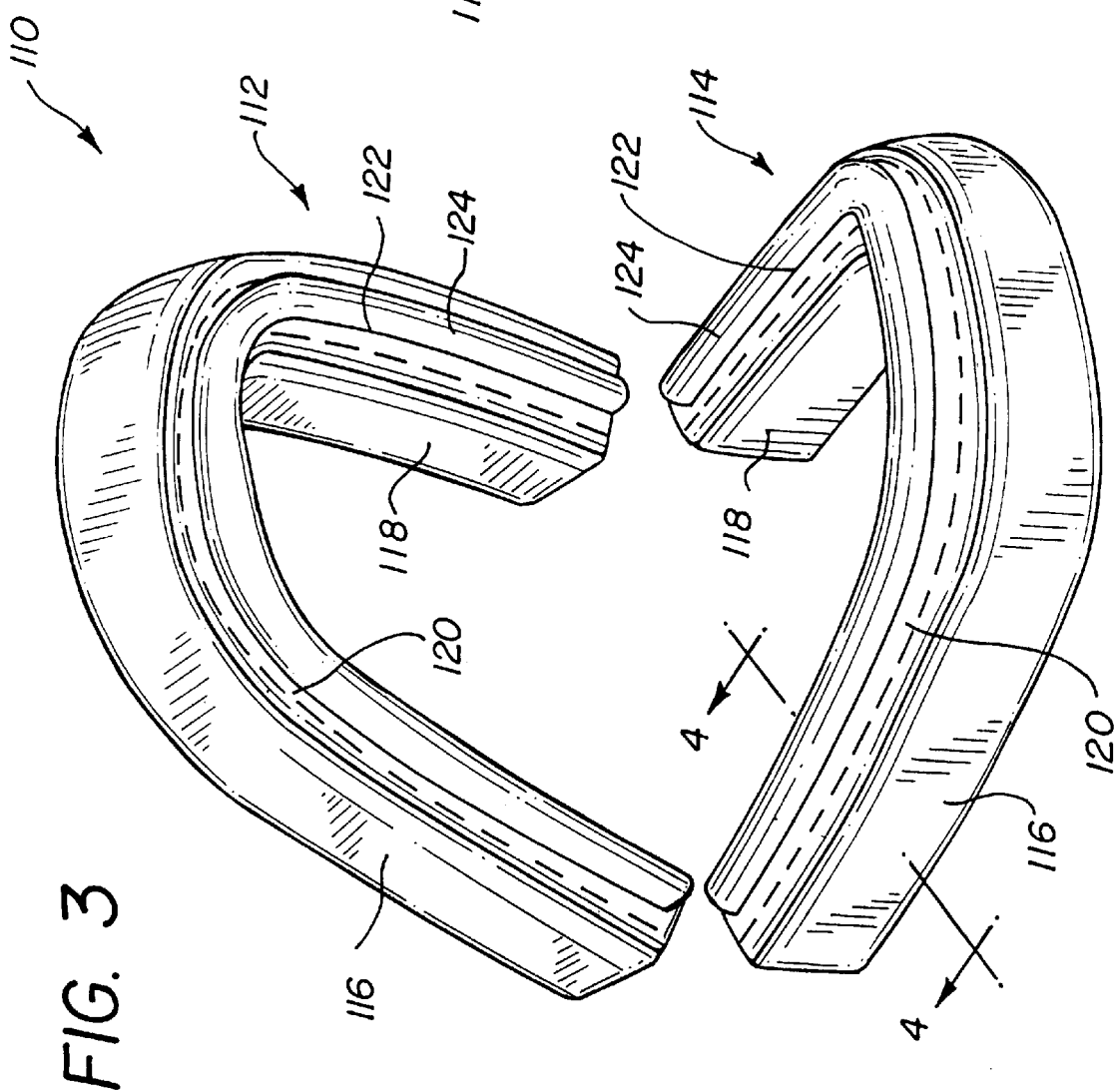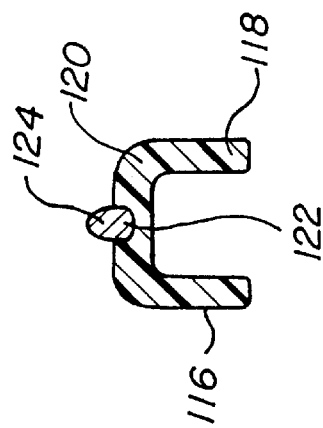

MOUTHGUARD MADE AT LEAST PARTIALLY FROM AN EDIBLE CANDY

BACKGROUND OF THE INVENTION

The present invention relates generally to a mouthguard that is positionable over the teeth of a person while performing oral sex, and more particularly, is directed to a mouthguard made at least partially of an edible candy.

A common complaint during fellatio is that the teeth scrape the penis, causing discomfort or pain. Although oral prophylactic devices are known for oral sex, these devices perform the function of preventing the spread of disease, such as the HIV virus, herpes and the like. As a result, they are made of an impermeable plastic or rubber material that must be washed after use and can be uncomfortable to wear and use. Further, the use of a plastic material which is relatively hard, can also cause discomfort.

For example, U.S. Pat. No. 4,949,731 to Harding discloses an oral prophylactic that may be flavored. In this patent, a tubular portion is received in the mouth and has a labial portion that fits over the person's lips. Both are also elastic and flexible to accommodate the natural range of movement of the lips, mouth and tongue. The purpose of the device is to prevent the spread of disease, such as AIDS. In this regard, the tubular portion is an impermeable body, and certainly, would not be edible, since this would be contrary to the teachings of the patent.

Other devices which disclose an oral prophylactic for oral-genital use, and which are intended to prevent the passage of venereal and other disease, and certainly could not be formed from an edible candy that dissolves during use, are disclosed in U.S. Pat. No. 5,318,043 to Burr et al; U.S. Pat. No. 5,409,016 to Bloodsaw; U.S. Pat. No. 5,582,187 to Hussey; and U.S. Pat. No. 5,657,765 to Est.

In addition to the above, when sucking on hard candy, such as lollipops, the teeth often hit the lollipop, resulting in chipping and breaking of the lollipop, contrary to the intended long term use thereof. The use of a mouthguard of the above types may not cure this defect. In any event, the sticky candy substance of a lollipop would have to be cleaned from the mouthguard after each use, and the mouthguard would not be comfortable in use.

OBJECTS AND SUMMARY OF THE INVENTION

Accordingly, it is an object of the present invention to provide a mouthguard that overcomes the problems with the aforementioned prior art.

It is another object of the present invention to provide a mouthguard made at least partially of an edible candy that does not cause discomfort or pain against a penis.

It is still another object of the present invention to provide a mouthguard made at least partially of an edible candy in which there is no clean-up.

It is yet another object of the present invention to provide a mouthguard made at least partially of an edible candy in which there is no waste.

It is a further object of the present invention to provide a mouthguard made at least partially of an edible candy that is easy and economical to use and make.

In accordance with an aspect of the present invention, a mouthguard includes an upper bite plate which removably fits over upper teeth of a person, the upper bite plate including an upper lingual side, an upper buccal side and a lower side which connects together the upper lingual and buccal sides, the lower side having a lower exposed surface, and the entire upper bite plate being made from a soft, deformable and edible material; and a lower bite plate which removably fits over lower teeth of the person, the lower bite plate including a lower lingual side, a lower buccal side and an upper side which connects together the lower lingual and buccal sides, the upper side having an upper exposed surface, and the entire lower bite plate being made from a soft, deformable and edible material.

Preferably, the edible material is a gummi candy made from corn syrup, sugar, gelatine and citric acid.

The upper bite plate has an overall U-shaped configuration and a substantially U-shaped cross-sectional configuration, and the lower bite plate has an overall U-shaped configuration and a substantially U-shaped cross-sectional configuration.

The upper bite plate and lower bite plate cover at least central incisor teeth, lateral incisor teeth, canine teeth and first pre-molar teeth. Alternatively, the upper bite plate and lower bite plate cover only at least central incisor teeth and lateral incisor teeth.

In accordance with another aspect of the present invention, a mouthguard includes an upper bite plate which removably fits over upper teeth of a person, the upper bite plate including an upper lingual side, an upper buccal side and a lower side which connects together the upper lingual and buccal sides, the lower side having a lower exposed surface, with a recess therein that travels along the lower exposed surface; a lower bite plate which removably fits over lower teeth of the person, the lower bite plate including a lower lingual side, a lower buccal side and an upper side which connects together the lower lingual and buccal sides, the upper side having an upper exposed surface, with a recess therein that travels along the upper exposed surface; and a soft, deformable and edible material removably positioned in each recess.

In such case, the edible candy has a substantially string-like shape that removably fits within the recess. As with the first embodiment, the edible material is preferably a gummi candy made from corn syrup, sugar, gelatine and citric acid.

The upper bite plate has an overall U-shaped configuration and a substantially U-shaped cross-sectional configuration, and the lower bite plate has an overall U-shaped configuration and a substantially U-shaped cross-sectional configuration.

Again, the upper bite plate and lower bite plate cover at least central incisor teeth, lateral incisor teeth, canine teeth and first pre-molar teeth, although they can be constructed to cover only at least central incisor teeth and lateral incisor teeth.

In accordance with still another aspect of the present invention, a mouthguard includes an upper bite plate which removably fits over upper teeth of a person, the upper bite plate including an upper lingual side, an upper buccal side and a lower side which connects together the upper lingual and buccal sides, the lower side having a lower exposed surface; a lower bite plate which removably fits over lower teeth of the person, the lower bite plate including a lower lingual side, a lower buccal side and an upper side which connects together the lower lingual and buccal sides, the upper side having an upper exposed surface; and at least a portion of the upper and lower exposed surfaces each having a soft, deformable and edible material thereat.

The above and other objects, features and advantages of the present invention will become readily apparent from the following detailed description thereof which is to be read in connection with the accompanying drawings.

BRIEF DESCRIPTION OF THE DRAWINGS

FIG. 1 is a perspective view of a mouthguard made at least partially of an edible candy according to a first embodiment of the present invention;

FIG. 2 is a cross-sectional view of the mouthguard of FIG. 1, taken along line 2—2 thereof;

FIG. 3 is a perspective view of a mouthguard made at least partially of an edible candy according to a second embodiment of the present invention;

FIG. 4 is a cross-sectional view of the mouthguard of FIG. 3, taken along line 4—4 thereof;

DETAILED DESCRIPTION OF THE PREFERRED EMBODIMENTS

Figure 6:
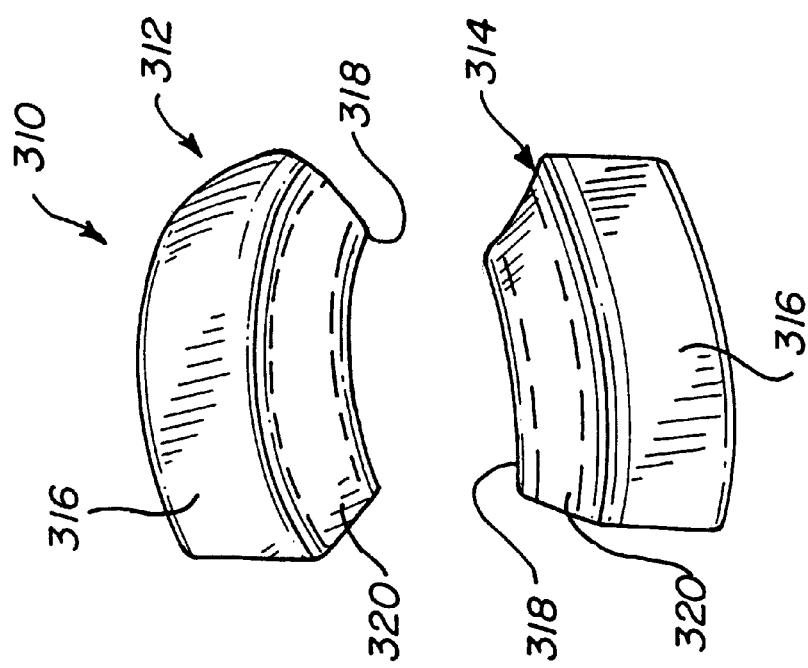
FIG. 6 is a perspective view of a mouthguard made at least partially of an edible candy according to a fourth embodiment of the present invention.

Referring to the drawings in detail, and initially to FIGS. 1 and 2, a mouthguard 10 according to a first embodiment of the present invention, includes an upper bite plate 12 which removably fits over the upper teeth of a person and a lower bite plate 14 which removably fits over the lower teeth of a person. An important aspect of the present invention is that the entire upper bite plate 12 and lower bite plate 14 are made from a soft, deformable, dissolvable and edible material. For example, a suitable material that can be used is a gummi candy commonly made, for example, from corn syrup, sugar, gelatine and citric acid.

Each bite plate 12 and 14 has a generally U-shape to fit over all of the teeth of a person, as shown in FIG. 1, with each bite plate 12 and 14 also having a U-shaped cross-sectional configuration, as shown in FIG. 2, so as to wrap about the buccal and lingual sides of the teeth. Thus, each bite plate 12 and 14 includes a U-shaped buccal side 16, a U-shaped lingual side 18, and a U-shaped connecting side 20 that connects buccal side 16 to lingual side 18 to complete the bite plate 12 or 14. The exposed surface of connecting side 20 is the surface that slides against the penis or lollipop, and the edges 20a and 20b thereof which connect with buccal side 16 and lingual side 20 are preferably rounded to eliminate sharp corners.

During oral sex, and particularly, fellatio, the gummi candy softens with the saliva of a person. Since the gummi candy covers the teeth, the penis or lollipop is protected against abrasion by the hard teeth. After oral sex or after eating the lollipop, bite plates 12 and 14 of mouthguard 10 are removed from the teeth and the gummi candy can be chewed and swallowed.

Thus, there is no damage to the penis or lollipop, there is no clean-up afterwards and there is no waste material.

Referring now to FIGS. 3 and 4, a mouthguard 110 according to a second embodiment of the present invention, includes an upper bite plate 112 which removably fits over the upper teeth of a person and a lower bite plate 114 which removably fits over the lower teeth of a person.

As with the first embodiment, each bite plate 112 and 114 of the second embodiment has a generally U-shape to fit over all of the teeth of a person, as shown in FIG. 3, with each bite plate 112 and 114 also having a U-shaped cross-sectional configuration, as shown in FIG. 4, so as to wrap about the buccal and lingual sides of the teeth. Thus, each bite plate 112 and 114 includes a U-shaped buccal side 116, a U-shaped lingual side 118, and a U-shaped connecting side 120 that connects buccal side 116 to lingual side 118 to complete the bite plate 112 or 114.

However, unlike the first embodiment, bite plates 112 and 114 are made from a plastic material that is not edible. The exposed surface of connecting side 120 of each bite plate 112 and 114 includes a groove or recess 122 centrally thereof, and because of the U-shape of connecting side 120, recess 122 also assumes a U-shape.

As with the first embodiment, an important aspect of the second embodiment of the present invention is that a soft, deformable, dissolvable and edible material slides along the penis or lollipop. Thus, a cylindrical or string-like strip 124 of such material is positioned in recess 122, and extends above the exposed surface of connecting side 120 of lower bite plate 114 and below the exposed surface of connecting side 120 of upper bite plate 112. For example, a suitable material that can be used for strip 124 is a gummi candy commonly made, for example, from corn syrup, sugar, gelatine and citric acid. Because of the sticky nature of strip 124 and because of the friction forces, strip 124 remains in recess 122 during any sliding action against the penis or lollipop.

During oral sex, and particularly, fellatio, the gummi candy of cylindrical strip 124 softens with the saliva of a person. Since the gummi candy of strip 124 extends above connecting side 120 of lower bite plate 114 and below connecting side 120 of upper bite plate 112 so as to slide on the penis or lollipop, the penis or lollipop is protected against abrasion by the hard teeth. After oral sex or after eating the lollipop, cylindrical strips 124 are removed from recesses 122 and the gummi candy thereof can be chewed and swallowed. Bite plates 112 and 114, however, are removed for future use.

Thus, there is no damage to the penis or lollipop, there is little clean-up afterwards and there is no waste material.

Figure 5:
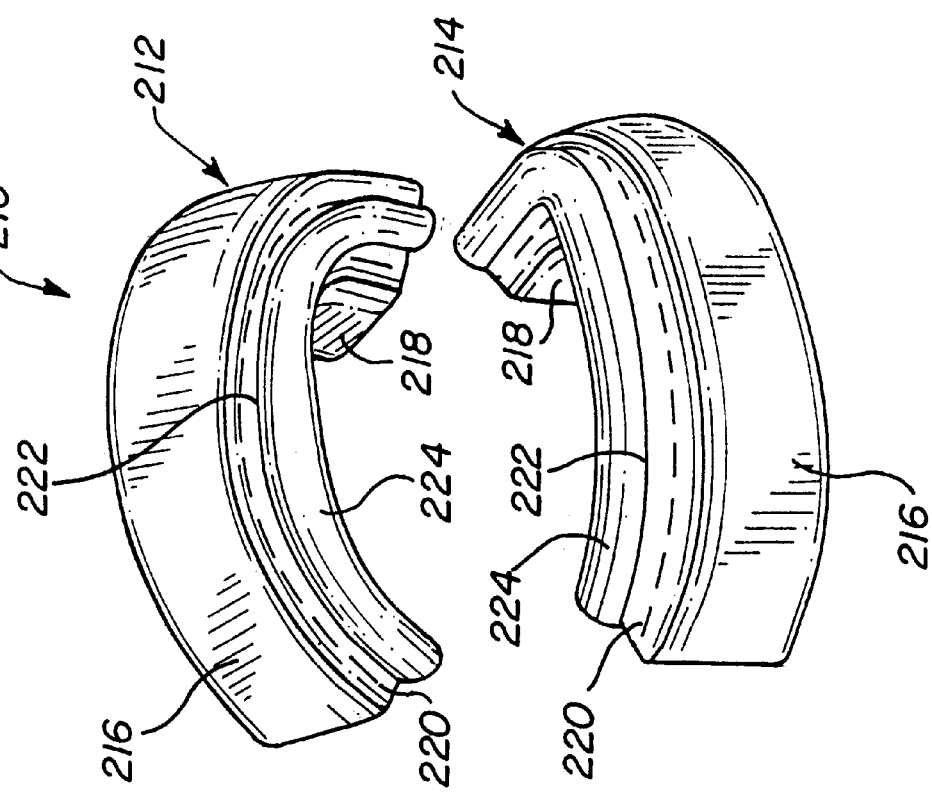
FIG. 5 is a perspective view of a mouthguard made at least partially of an edible candy according to a third embodiment of the present invention.

It will be appreciated that it is only important that the mouthguard generally protect against abrasion from the central and lateral incisors, and possibly, the canine teeth. In this regard, as shown in FIG. 5, a mouthguard 210 is shown which is identical to mouthguard 110, but which is truncated to cover only the central incisors, lateral incisors, canine and first pre-molar teeth. In such case, mouthguard 210 includes an upper bite plate 212 and a lower bite plate 214, each with a U-shaped buccal side 216, a U-shaped lingual side 218 and a U-shaped connecting side 220, with a groove or recess 222 in the exposed surface of connecting side 220 and a cylindrical strip 224 formed by a soft, deformable, dissolvable and edible material in recess 222, with the above elements being in truncated form.

The mouthguard can be truncated even further so as to cover only the central and lateral incisors, as shown by mouthguard 310 of FIG. 6, which is identical to mouthguard 10, but truncated. In such case, mouthguard 310 includes an upper bite plate 312 and a lower bite plate 314, each with a U-shaped buccal side 316, a U-shaped lingual side 318 and a U-shaped connecting side 320, the entire mouthguard 310 being made from a soft, deformable, dissolvable and edible material, and with the above elements being in truncated form.

The key to the invention is that at least part of the mouthguard is made from a gummi candy or other soft, edible material. The reason is to protect against the teeth hitting the penis during oral sex, or to protect the lollipop during sucking of the same. At the same time, however, the gummi candy is edible and dissolvable so that it can be eaten after. Thus, there is no damage to the penis or lollipop, there is little or no clean-up afterwards and there is no waste.

Having described specific preferred embodiments of the invention with reference to the accompanying drawings, it will be appreciated that the present invention is not limited to those precise embodiments, and that various changes and modifications can be effected therein by one of ordinary skill in the art without departing from the scope or spirit of the invention as defined by the appended claims.

What is claimed is:

1. A mouthguard comprising:

an upper bite plate which removably fits over upper teeth of a person, the upper bite plate including an upper lingual side, an upper buccal side and a lower side which connects together the upper lingual and buccal sides, the lower side having a lower exposed surface, and the entire upper bite plate being made from a soft, deformable and edible material; and a lower bite plate which removably fits over lower teeth of the person, the lower bite plate including a lower lingual side, a lower buccal side and an upper side which connects together the lower lingual and buccal sides, the upper side having an upper exposed surface, and the entire lower bite plate being made from a soft, deformable and edible material each of said upper and lower bite plates having a substantially U-shape transverse cross sectional configuration.

2. A mouthguard according to claim 1, wherein said edible material is a gummi candy.

3. A mouthguard according to claim 2, wherein said gummi candy is made from a material selected from the group consisting of corn syrup, sugar, gelatine and citric acid.

4. A mouthguard according to claim 1, wherein:

said upper bite plate has an overall U-shaped configuration and a substantially U-shaped cross-sectional configuration, and said lower bite plate has an overall U-shaped configuration and a substantially U-shaped cross-sectional configuration.

5. A mouthguard according to claim 1, wherein said upper bite plate and lower bite plate cover at least central incisor teeth, lateral incisor teeth, canine teeth and first pre-molar teeth.

6. A mouthguard according to claim 1, wherein said upper bite plate and lower bite plate cover at least central incisor teeth and lateral incisor teeth.

7. A mouthguard comprising:

an upper bite plate which removably fits over upper teeth of a person, the upper bite plate including an upper lingual side, an upper buccal side and a lower side which connects together the upper lingual and buccal sides, the lower side having a lower exposed surface, with a recess therein that travels along said lower exposed surface;

a lower bite plate which removably fits over lower teeth of the person, the lower bite plate including a lower lingual side, a lower buccal side and an upper side which connects together the lower lingual and buccal sides, the upper side having an upper exposed surface, with a recess therein that travels along said upper exposed surface; and a soft, deformable and edible material removably positioned in each said recess.

8. A mouthguard according to claim 7, wherein said edible candy has a substantially string shape that removably fits within said recess.

9. A mouthguard according to claim 7, wherein said edible material is a gummi candy.

10. A mouthguard according to claim 9, wherein said gummi candy is made from a material selected from the group consisting of corn syrup, sugar, gelatine and citric acid.

11. A mouthguard according to claim 7, wherein:

said upper bite plate has an overall U-shaped configuration and a substantially U-shaped cross-sectional configuration, and said lower bite plate has an overall U-shaped configuration and a substantially U-shaped cross-sectional configuration.

12. A mouthguard according to claim 7, wherein said upper bite plate and lower bite plate cover at least central incisor teeth, lateral incisor teeth, canine teeth and first pre-molar teeth.

13. A mouthguard according to claim 7, wherein said upper bite plate and lower bite plate cover at least central incisor teeth and lateral incisor teeth.

14. A mouthguard comprising:

an upper bite plate which removably fits over upper teeth of a person, the upper bite plate including an upper lingual side, an upper buccal side and a lower side which connects together the upper lingual and buccal sides, the lower side having a lower exposed surface;

a lower bite plate which removably fits over lower teeth of the person, the lower bite plate including a lower lingual side, a lower buccal side and an upper side which connects together the lower lingual and buccal sides, the upper side having an upper exposed surface; and at least a portion of the upper and lower exposed surfaces each having a soft, deformable and edible material thereat, each of said upper and lower bite plates having a substantially U-shape transverse cross sectional configuration.

* * * * *